United States Patent
Roth et al.

[11] Patent Number: 5,843,286
[45] Date of Patent: Dec. 1, 1998

[54] PROCESS FOR THE PREPARATION AND FRACTIONATION OF A MIXTURE OF DIMETHYL ETHER AND CHLOROMETHANE WITH WATER AS EXTRACTANT

[75] Inventors: Peter Roth, Eppstein; Erhard Leistner, Braunfels; Hans Haverkamp, Eppstein, all of Germany

[73] Assignee: Hoechst Aktiengesellschaft, Germany

[21] Appl. No.: 880,607

[22] Filed: Jun. 23, 1997

[30] Foreign Application Priority Data

Jun. 25, 1996 [DE] Germany .................. 196 25 283.0

[51] Int. Cl.⁶ .................. B01D 3/38; C07C 17/386; C07C 41/42

[52] U.S. Cl. .................. 203/18; 203/78; 203/79; 203/80; 203/DIG. 23; 570/262; 568/699

[58] Field of Search .................. 203/18, 78, 79, 203/80, DIG. 9, 92–98, DIG. 23; 568/579, 697, 699; 570/258, 262

[56] References Cited

U.S. PATENT DOCUMENTS

| | | | |
|---|---|---|---|
| 2,421,441 | 6/1947 | Thronson et al. | 570/263 |
| 3,847,756 | 11/1974 | Statman et al. | 203/92 |
| 3,983,180 | 9/1976 | Habata et al. | 570/258 |
| 4,220,609 | 9/1980 | McEntee et al. | 570/258 |
| 4,334,964 | 6/1982 | Prezelj et al. | 203/14 |
| 4,349,416 | 9/1982 | Brandt et al. | 203/DIG. 13 |
| 4,544,776 | 10/1985 | Osterburg et al. | 568/697 |
| 4,560,807 | 12/1985 | Murai et al. | 568/698 |
| 4,794,204 | 12/1988 | Post et al. | 570/262 |
| 5,092,966 | 3/1992 | Berg et al. | 203/57 |
| 5,122,236 | 6/1992 | Smith, Jr. et al. | 203/92 |
| 5,132,476 | 7/1992 | Osterburg et al. | 570/258 |
| 5,430,197 | 7/1995 | Jones, Jr. | 568/697 |
| 5,609,734 | 3/1997 | Streiber et al. | 203/98 |

FOREIGN PATENT DOCUMENTS

| | | |
|---|---|---|
| 0 039 001 | 11/1981 | European Pat. Off. . |
| 0 124 078 | 11/1984 | European Pat. Off. . |

OTHER PUBLICATIONS

Database WPI Section Ch, Week 8036, Derwent Publication Ltd., London, GB & DD 142 183 A (Berger K H), Jun. 11, 1980.

Database WPI Section Ch, Week 8036, Derwent Publication Ltd., London, GB & DD 142 183 A (Berger K H), Jun. 11, 1980.

*Primary Examiner*—Virginia Manoharan
*Attorney, Agent, or Firm*—Connolly & Hutz

[57] ABSTRACT

A process for the preparation and fractionation of a mixture of dimethyl ether and chloromethane by extractive distillation with water as extractant. The mixture is prepared by reacting methanol with hydrogen chloride. It is then subjected to an extractive distillation with water as extractant, resulting in chloromethane as top product. In the next step, the dimethyl ether is removed by distillation and, in another step, the extraction water is separated from the methanol which is still present.

14 Claims, 1 Drawing Sheet

PROCESS FOR THE PREPARATION AND FRACTIONATION OF A MIXTURE OF DIMETHYL ETHER AND CHLOROMETHANE WITH WATER AS EXTRACTANT

DESCRIPTION

A process for the preparation and fractionation of a mixture of dimethyl ether and chloromethane with water as extractant.

The present invention relates to a process for the preparation of a mixture of dimethyl ether and chloromethane, and to the fractionation thereof by means of extractive distillation with water as extractant.

Chloromethane is industrially important as starting material for the preparation of chlorofluorocarbons which are then used as propellant gases in aerosol packs. Dimethyl ether is increasingly being used as propellant in aerosol packs because it is halogen-free and thus has less potential to degrade ozone.

Both compounds are produced as shown in equations (I) and (II) in the reaction of methanol with HCl, which is frequently carried out industrially on $\gamma$-$Al_2O_3$ catalysts to increase the reaction rate:

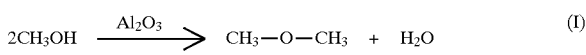

In the previous prior art it was customary to regard the dimethyl ether produced in the preparation of chloromethane as waste, and to dispose of it by hydrolysis with sulfuric acid. However, since dimethyl ether is valuable because it can be used as propellant, there was a need for a process which makes it possible to exploit industrially the unavoidable production of dimethyl ether.

The mixture of dimethyl ether and chloromethane cannot be worked up by distillation according to the prior art because the boiling points of the components are very close to one another (dimethyl ether boiling point=$-24.9°$ C., chloromethane boiling point=$-23.7°$ C.), and moreover the components form an azeotrope.

The object was thus to develop a preparation and fractionation process which affords both pure dimethyl ether and pure chloromethane.

This object has been achieved according to the invention by a two-stage synthetic process with subsequent three-stage workup process which comprises an extractive distillation with water.

The invention thus relates to a process for the preparation and fractionation of a mixture of dimethyl ether and chloromethane, which comprises a) reacting methanol with an excess of HCl, b) reacting the mixture obtained in step a) with an excess of methanol, c) feeding the mixture obtained in step b) to an extractive distillation column, d) adding water as extractant in the upper part of the extractive distillation column, e) taking off chloromethane from the top of the extractive distillation column, f) taking off a mixture of water, methanol and dimethyl ether from the bottom of the extractive distillation column and feeding it to a first distillation column, g) taking off dimethyl ether from the top of the first distillation column, h) taking off a mixture of water and methanol from the bottom of the first distillation column, i) feeding the mixture obtained in step h) into a second distillation column, k) taking off pure methanol at the top of the second distillation column, l) taking off water at the bottom of the second distillation column, m) feeding the methanol obtained in step k) into the reactions mentioned in steps a) and b).

It is preferred to use a catalyst for the esterification reaction described in steps a) and b). Suitable examples are $\gamma$-$Al_2O_3$ catalysts.

Delivery of the mixture described in step c) preferably takes place by liquefying the mixture, which results as a gas, in a condenser, delivering the condensate with a pump and vaporizing it again before entry into the extractive distillation column.

The extractive distillation is preferably carried out under pressures between 1 and 25 bar. All the columns used can be of any suitable design, and packed columns are preferably used.

In one embodiment of the invention, the extractive distillation column is operated so that dimethyl ether and methanol can be taken off at the top in step g). The product stream obtained in this way is partly taken off and fed into the reaction described in steps a) and b). This embodiment allows the ratio of the amounts of chloromethane and dimethyl ether produced to be influenced by shifting the equilibrium.

DESCRIPTION OF THE PREFERRED EMBODIMENT

Figure 1:
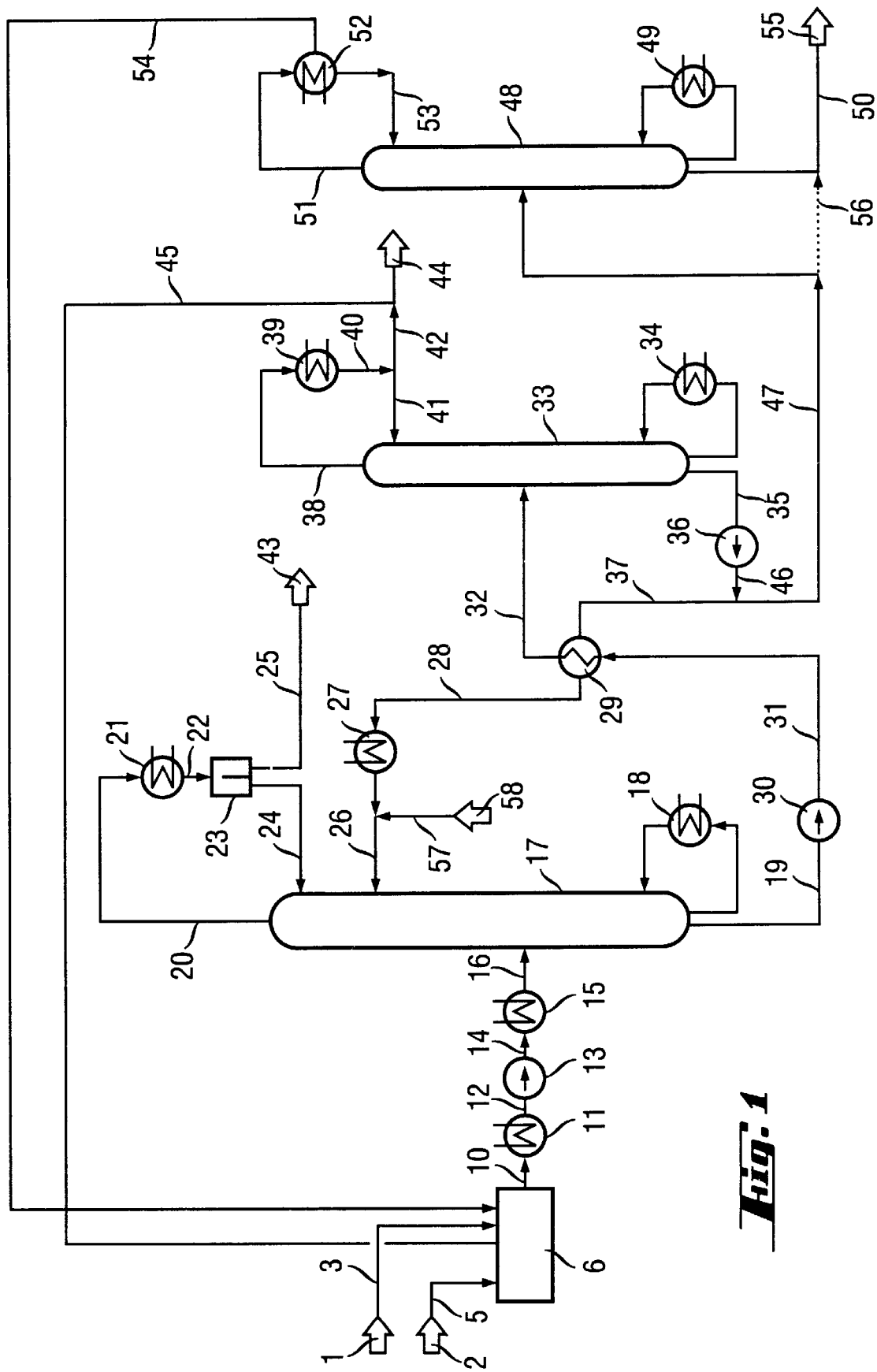
FIG. 1 is a flow diagram for a preferred embodiment of the process according to the invention.

Methanol (1) vapor is fed through line (3) into a two-stage esterification reactor (6). In addition, gaseous HCl (2) is fed through line (5) into the reactor. The two-stage esterification reactor can be designed in the form of a two-stage tubular reactor. In the first stage, HCl and methanol are added to the reactor. The amounts of the reactants are such that the amount of substance for HCl is up to 20% above the stoichiometric amount of substance necessary for the reaction with the methanol. The mixture of HCl and methanol flows through the first stage of the reactor, which can be charged with a catalyst. In the case of a gas-phase reaction, the reaction is exothermic so that cooling should be provided for both stages of the reactor. The mixture of chloromethane, water and HCl leaving the first stage of the reactor is mixed with an amount of methanol which is up to 20% above the amount of substance stoichiometrically necessary for reaction with the HCl present in the mixture. The mixture flows through the second stage of the reactor, which may likewise be charged with a catalyst. The reaction can be carried out with liquid or gaseous reactants. The reactions indicated in equations (I) and (II) take place in the reactor (6). The mixture consisting of dimethyl ether, chloromethane, methanol and water which leaves the reactor is then passed into the extractive distillation column (17). The mixture is preferably passed through line (10) into a condenser (11) and liquefied there, after which it passes through line (12), a pump (13)

and line (14) to a vaporizer (15), before it is fed through line (16) into the extractive distillation column (17). Dimethyl ether and chloromethane are separated in the extractive distillation column (17), the bottom of which is heated by means of the vaporizer (18). Water is added as extractant, which is preferably at a temperature between 5° and 50° C., through line (26) to the upper part of the extractive distillation column (17). Water precipitates dimethyl ether in the bottom, while chloromethane is taken off as vapor at the top through line (20) and, where appropriate, fed to the condenser (21). If the vapor at the top contains large amounts of water, which depends on the operating conditions for the extractive distillation column (17), the condensate can be passed through line (22) into a phase separator (23). If a phase separator is used, the aqueous phase is returned through line (24) to the top of the extractive distillation column (17). Chloromethane is then fed through line (25) to the product store (43). If no phase separator is used, part of the condensate can be returned through line (24) as reflux to the top of the extractive distillation column (17), and the remaining part is taken off and fed through line (25) to the product store (43). A mixture of methanol, dimethyl ether and water collects in the bottom of the extractive distillation column (17). This is fed through line (19), pump (30) and line (31) where appropriate to a heat exchanger (29) in which it is heated, and passes from there through line (32) to the first distillation column (33) in which dimethyl ether is removed. Dimethyl ether vapor is taken off at the top through line (38) and, where appropriate, fed to a condenser (39). From there, part of it may pass through lines (40) and (41) as reflux back to the top of the first distillation column (33), otherwise it is taken off through line (42) and fed to the product store (44). A mixture of methanol and water collects in the bottom of first distillation column (33), which is heated via the vaporizer (34). This mixture is fed through line (35) to a pump (36) and passes from there through line (46) where appropriate partly through line (37) to the heat exchanger (29), where it is cooled, and where appropriate from there through line (28) into the cooler (27), where further cooling takes place. From there it is again added as extractant through line (26) to the extractive distillation column (17). For starting up the system and for compensating losses, fresh water (58) is fed through line (57). The remaining part of the bottom product from the first distillation column (33) is fed through line (47) to a second distillation column (48) in which methanol and water are separated. The second distillation column is preferably operated under atmospheric pressure. Pure methanol vapor is taken off from the top of the second distillation column (48) through line (51). This can be liquefied in the condenser (52) and partly returned through line (53) to the top of the second distillation column (48). The remaining part of the methanol is fed through line (54) to the esterification reactor (6). Pure water (55) collects in the bottom of the second distillation column (48). This is drawn off through line (50). The bottom of the second distillation column (48) is heated via the vaporizer (49).

It is possible in a particular embodiment of the invention to prepare chloromethane exclusively. This is done by operating the first distillation column (33) in such a way that dimethyl ether and methanol are distilled out. The resulting mixture is fed through line (45) to the esterification reactor (6) where mainly chloromethane is produced due to a shift in the reaction equilibrium. Part of the water of reaction emerging from the first distillation column is then taken off directly through lines (47), (56) and (50). In this specific embodiment of the invention, the second distillation column (48) is unnecessary.

The following table summarizes the top and bottom temperatures, in °C., occurring in the columns in the preferred pressure range.

| Column | 1 bar | | 25 bar | |
| --- | --- | --- | --- | --- |
|  | Top | Bottom | Top | Bottom |
| (17) | −24 | 90 | 90 | 200 |
| (33) | −25 | 100 | 85 | 224 |
| (48) | 64 | 100 | 180 | 224 |

EXAMPLE 7.1 t/h methanol and 5.3 t/h HCl are fed into an esterification reactor (6). The two-stage reaction at 250° C. under a pressure of 4 bar using a $\gamma$-$Al_2O_3$ catalyst produces a reaction gas of the following composition:

dimethyl ether: 1.8 t/h methanol: 0.01 t/h chloromethane: 7.3 t/h $H_2O$: 3.29 t/h This reaction gas is completely liquefied in a condenser (11) under about 4 bar and at a minimum temperature of about 10° C. The resulting condensate is delivered by the pump (13) into the vaporizer (15). The condensate is partially vaporized here under 10 bar and at about 100° C. It is possible to use as heating medium for this purpose the heat of condensation liberated in the condenser (11). The vapor/liquid mixture from (15) is completely fed into the extractive distillation column (17). This is likewise operated under a pressure of 10 bar.

If, for unforeseen reasons, HCl were to occur in the reaction gas, this can be neutralized in the condenser (11) using aqueous sodium hydroxide solution. In the extractive distillation column (17), dimethyl ether is dissolved in about 36 t/h extraction water with a methanol content of about 2.4% by weight. Since a certain amount of chloromethane also dissolves in the extractant, this is stripped out in the lower part of the column.

Heating is effected with heating steam via the vaporizer (18). The bottom product from the extractive distillation is a mixture consisting of:

1.8 t/h dimethyl ether 0.9 t/h methanol 39.0 t/h water.

The chloromethane content in this product stream is about 1 ppm.

The liquid top product from the extractive distillation column (17) is 7.3 t/h chloromethane with a dimethyl ether content of less than 20 ppm. The extraction water must be fed in as cold as possible through line (26), preferably at about 35° C. The temperature at the top of the extractive distillation column (17) is about 40° C., which makes it possible to condense the top product with recycled cooling water. The bottom temperature is about 124° C., so that heating with low pressure steam is possible.

The discharge from the bottom of the extractive distillation column (17) is, with the aid of the pump (30), preheated in the heat exchanger (29) and fed into the column (33). This is likewise operated under 10 bar. The top product in this case is about 1.8 t/h liquid dimethyl ether at about 40° C. The chloromethane content in the dimethyl ether is less than 20 ppm. The bottom product from the first distillation column (33) is a mixture consisting of about 40 t/h water with a methanol content of about 2.4% by weight. Most of it (about 36 t/h) is, after cooling to about 35° C., again fed into the extractive distillation column (17). A part-stream of the bottom product from the first distillation column (33) is introduced into the second distillation column (48). Methanol is separated from water here under a pressure of 1 bar. Methanol (about 0.01 t/h) is obtained as top product here and is again fed into the reaction (6). The bottom product is water (about 3.9 t/h) with a methanol content of about 0.08% by weight.

We claim:

1. A process for the preparation and fractionation of a mixture of dimethyl ether and chloromethane, which comprises
   a) reacting methanol with an excess of HCl,
   b) reacting the mixture obtained in step a) with an excess of methanol,
   c) feeding the mixture obtained in step b) to an extractive distillation column,
   d) adding water as extractant in the upper part of the extractive distillation column,
   e) taking off chloromethane from the top of the extractive distillation column,
   f) taking off a mixture of water, methanol and dimethyl ether from the bottom of the extractive distillation column and feeding it to a first distillation column,
   g) taking off dimethyl ether from the top of the first distillation column,
   h) taking off a mixture of water and methanol from the bottom of the first distillation column,
   i) feeding the mixture obtained in step h) into a second distillation column,
   k) taking off methanol at the top of the second distillation column,
   l) taking off water at the bottom of the second distillation column,
   m) feeding the methanol obtained in step k) into the reactions mentioned in steps a) and b).

2. The process as claimed in claim 1, wherein the chloromethane and dimethylether obtained in steps e) and g) are condensed before being used further.

3. The process as claimed in claim 1, wherein chloromethane emerging from the top of the extractive distillation column in step e) undergoes a phase separation.

4. The process as claimed in claim 1, wherein the reaction mixture fed in step c) is a gas, first condensed and then vaporized again.

5. The process as claimed in claim 1, wherein the extractive distillation is carried out under pressures between 1 and 25 bar.

6. The process as claimed in claim 1, wherein all the columns used are packed columns.

7. The process as claimed in claim 1, wherein the extraction water is at a temperature between 5° and 50° C. when fed into the extractive distillation in step d).

8. The process as claimed in claim 1, wherein the mixture in step f) is heated before addition to the first distillation column, and wherein the mixture in step h) is cooled before addition to the second distillation column.

9. The process as claimed in claim 8, wherein the heating of the mixture takes place in a heat exchanger, and wherein the cooling of the mixture likewise takes place in the heat exchanger.

10. The process as claimed in claim 1, wherein the reaction in steps a) and b) is carried out with the aid of a catalyst.

11. The process as claimed in claim 1, wherein the HCl and methanol in steps a) and b) are up to 20% of the stoichiometric amounts required for the reaction.

12. The process as claimed in claim 1, wherein part of the chloromethane obtained in step e) is returned to the top of the extractive distillation column.

13. The process as claimed in claim 1 wherein part of the dimethylether product obtained in step g) is returned to the top of the first distillation column.

14. The process as claimed in claim 1 wherein the methanol obtained in step k) is partly fed to the top of the second distillation column.

* * * * *

UNITED STATES PATENT AND TRADEMARK OFFICE
CERTIFICATE OF CORRECTION

PATENT NO. : 5,843,286
DATED : December 1, 1998
INVENTOR(S) : Peter Roth et al.

It is certified that error appears in the above-identified patent and that said Letters Patent is hereby corrected as shown below:

Column 6, line 2 (Claim 2, line 2), "dimethylether" should read -- dimethyl ether --;

and line 34, (Claim 13, line 2) "dimethylether product" should read -- dimethyl ether --.

Signed and Sealed this

Sixteenth Day of March, 1999

Attest:

Q. TODD DICKINSON

*Attesting Officer*      *Acting Commissioner of Patents and Trademarks*